United States Patent [19]

Taylor et al.

[11] Patent Number: 5,397,323
[45] Date of Patent: Mar. 14, 1995

[54] REMOTE CENTER-OF-MOTION ROBOT FOR SURGERY

[75] Inventors: Russell H. Taylor, Yorktown; Janez Funda, Valhalla; David D. Grossman, Chappaqua; John P. Karidis, Ossining; David A. LaRose, Croton on Hudson, all of N.Y.

[73] Assignee: International Business Machines Corporation, Armonk, N.Y.

[21] Appl. No.: 968,715

[22] Filed: Oct. 30, 1992

[51] Int. Cl.$^6$ .............................................. A61B 19/00
[52] U.S. Cl. ...................................... 606/130; 901/48; 901/41
[58] Field of Search ..................... 606/130, 88; 901/48, 901/15, 41; 414/719, 917, 728, 718

[56] References Cited

U.S. PATENT DOCUMENTS

| | | | |
|---|---|---|---|
| 4,140,226 | 2/1979 | Richter | 901/48 |
| 4,592,352 | 6/1986 | Patil . | |
| 4,638,799 | 1/1987 | Moore | 606/130 |
| 4,788,482 | 11/1988 | Tachibana et al. | 901/15 |
| 4,975,016 | 12/1990 | Pellenc et al. | 414/917 |
| 5,100,411 | 3/1992 | Koutrouvelis | 606/130 |

FOREIGN PATENT DOCUMENTS 482439 1/1970 Switzerland ........................ 606/130

OTHER PUBLICATIONS

J. P. Trevelyan et al., "Motion Control for a Sheep Shearing Robot", Proc. First Int'l. Symposium of Robotics Research, copyright 1984, MIT Press, Cambridge, Mass., pp. 175–190.

H. Asada et al., "Development of a Direct-Drive Arm Using High Torque Brushless Motors", Proc. First Int'l Symp. of Rob. Research, copyright 1984, MIT Press, Cambridge, Mass., pp. 583–599.

H. Kazerooni, "Design and Analysis of the Statically Balanced Direct-Drive Robot Manip . . ." Robotics & Comp. Integrated Manuf., vol. 6, No. 4 pp. 287–293, 1989, printed in GreatBritain.

*Primary Examiner*—Tamara L. Graysay
*Attorney, Agent, or Firm*—Louis J. Percello

[57] ABSTRACT

An apparatus used to assist a surgeon in surgery is divided into two parts, proximal and distal. The apparatus has a number of rigid links which rotate about pivots to position and re-position an instrument, like a surgical instrument, at a work point proximal to a patient but remote from the apparatus. The links cooperate in a way to move the manipulator about a center-of-motion with orthogonally decoupled degrees of freedom resolved at the work point.

The proximal part of the apparatus is adjustably fixed to a stationary object, like an operating table, while the distal part of the apparatus holds the instrument. Certain links which can be adjusted in length, move the distal part with respect to the proximal part of the apparatus. In this manner, the work point of the manipulator and the working radius of the apparatus are changed without moving the proximal part. Actuators, manual or remotely (computer) controlled, both rotate the links about their pivots and adjust the length of the adjustable links. All the actuators can be mounted on the proximal part of the apparatus and electrically isolated from the manipulator in order to reduce the shock hazard to the patient.

41 Claims, 11 Drawing Sheets

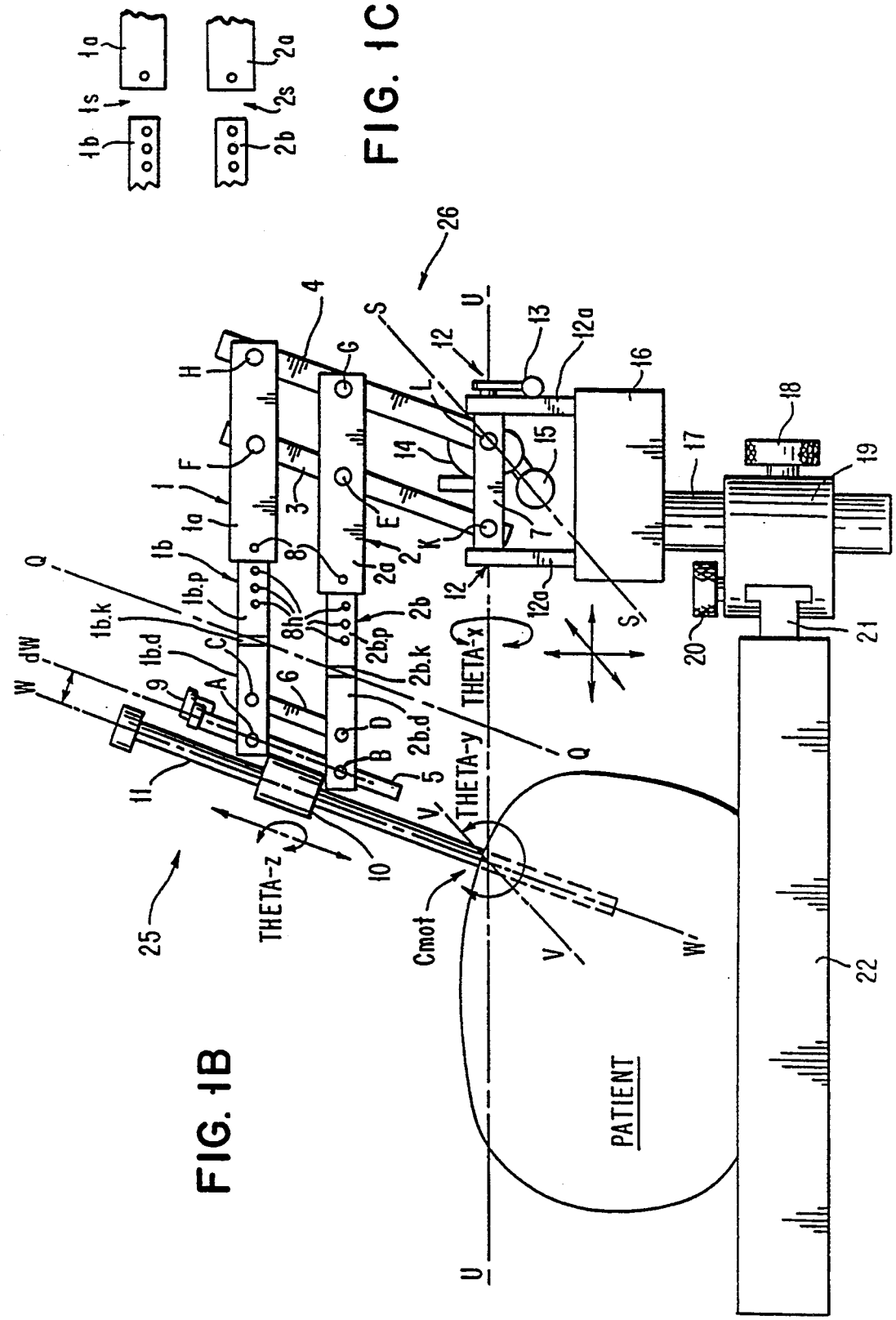

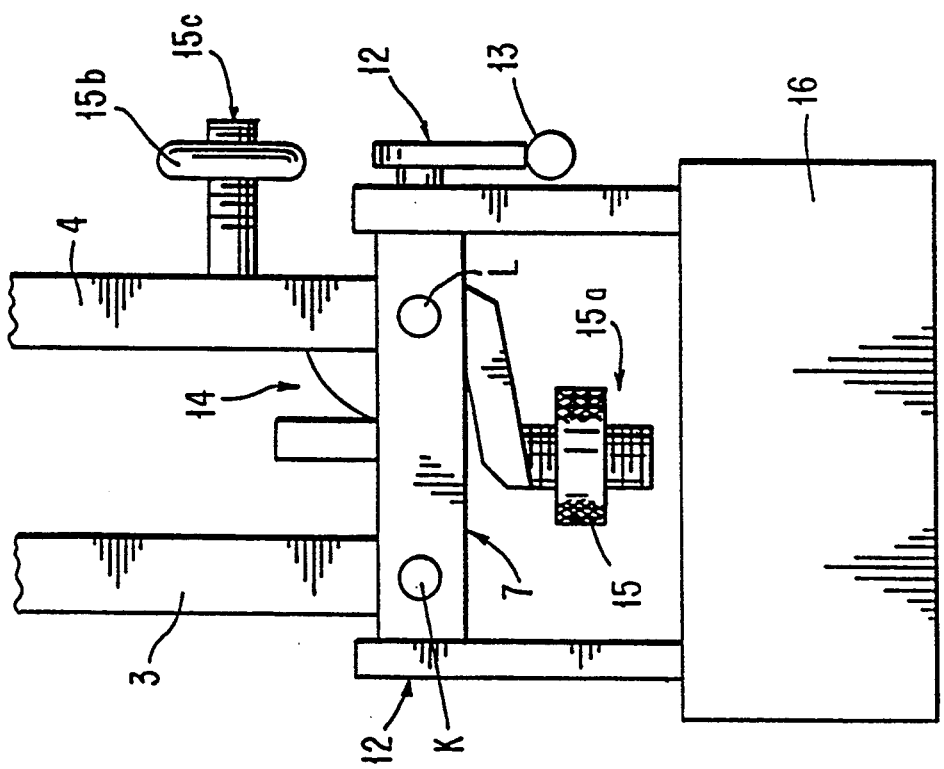
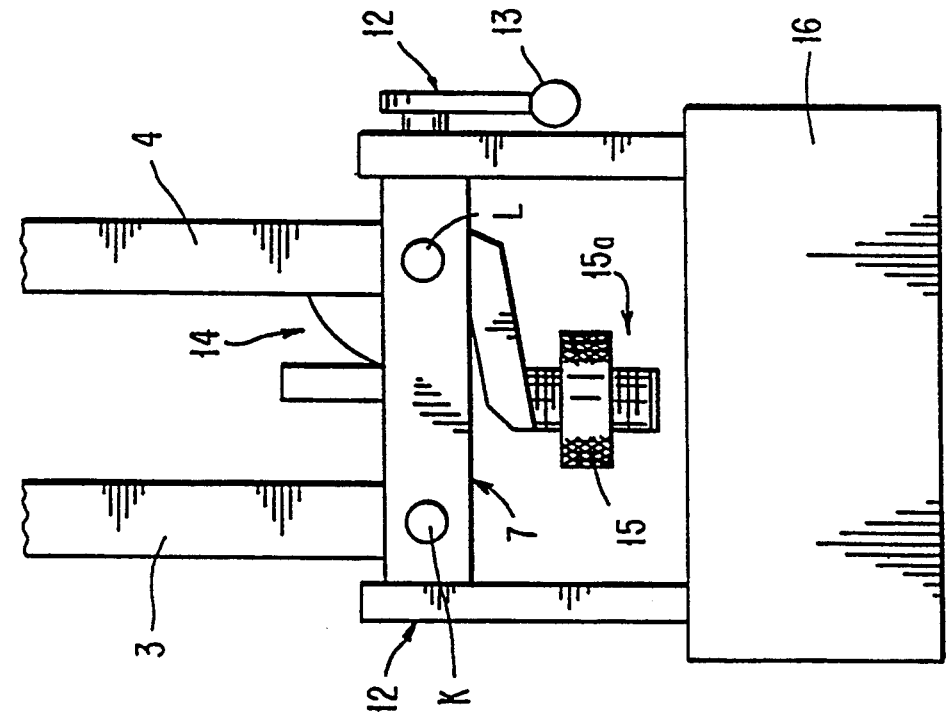

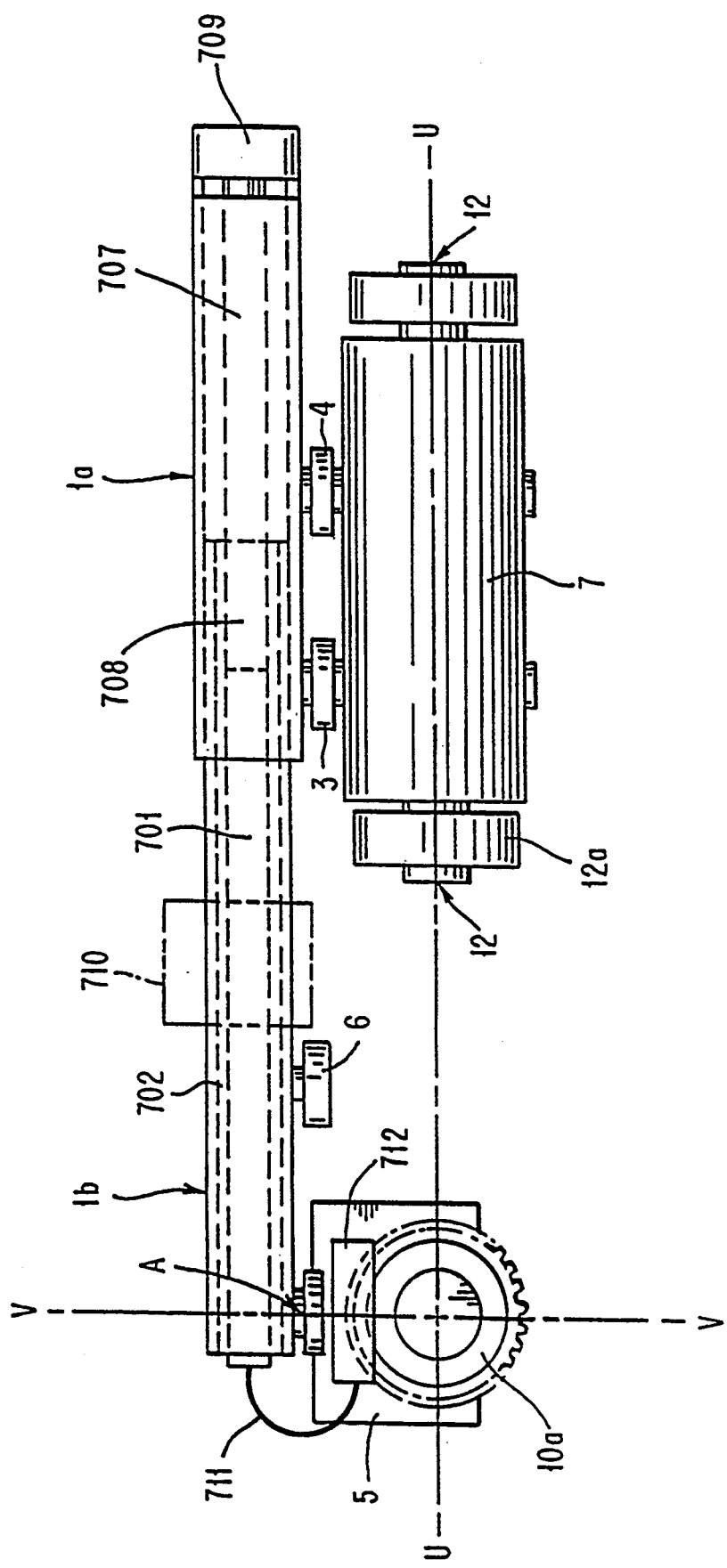

REMOTE CENTER-OF-MOTION ROBOT FOR SURGERY

FIELD OF THE INVENTION

This invention relates to the field of robotics, in particular to the use of robots in surgery.

BACKGROUND OF THE INVENTION

U.S. patent application Ser. No. 07/714,816 filed Jun. 13, 1991 by R. H. Taylor et al., and herein incorporated by reference, disclosed a system for the augmentation of surgery with a remote center-of-motion manipulator structure with orthogonally decoupled degrees of freedom resolved at a work point frame distal to the manipulator structure. In such a mechanism, successive axes of revolute motion are perpendicular to each other and intersect at the work point, and the linear motion axes are similarly perpendicular. This orthogonal decoupling at a remote tool frame has many advantages for surgical applications, both in "passive" and "active" embodiments of the structure.

In passive embodiments, each manipulator degree-of-freedom may be equipped with a brake but all motive force is provided by a human surgeon. In typical applications, the surgeon wishes to manipulate a surgical tool, tool guide, or piece of the patient's anatomy (such as a bone fragment) so that a desired spatial relationship relative to the patient or equipment in the operating room is achieved. Since each motion axis of the mechanism only affects one rotational or translational degree of freedom of a bone fragment or other object rigidly held at the work point, this structure permits the surgeon to work on only one or two degrees of freedom at a time without disturbing those which have already been aligned, thus greatly simplifying his alignment task while allowing him (or her) to work in a coordinate system that is natural and intuitively understandable for the task at hand.

In active embodiments, a computer controlled actuator drives one or more of the motion axes. Typical surgical applications include manipulation of laparoscopic cameras, precise tissue removal, biopsy sampling, and the like. Many of these applications require accurately controlled motion under computer control, often involving reorientation of a tool, while strictly limiting undesired motions. Further, many of these applications only require relatively slow precise computer-controlled motions, with somewhat more rapid approximate gross motions, which may be done passively.

In the example of laparoscopic camera manipulation, for example, the principal requirements for the manipulation system include safety, the ability to limit lateral motion at the point where the camera enters the body, the ability to rapidly achieve an approximate gross position of the camera, and the ability to make precise, calibrated motions of the camera under control of the computer.

An orthogonally decoupled remote center-of-motion (RCM) structure has many advantages for filling these requirements, as compared to a traditional industrial robot for which the design point is typically the ability to move rapidly through a large work volume with a compact (usually serial-link) mechanical structure. In a conventional industrial robot, motions about a remote motion center are achieved by coordinated motions of multiple joints, many of which may be required to make fairly large motions in order to achieve relatively small tool reorientations. If the joints are fast enough to achieve these motions in reasonable time, they are also typically fast enough to cause quite rapid end effector motion when the manipulator is at a different position. Put another way, if the joint actuators (motors and transmission ratios) are sized so as to limit the maximum possible speed of the tool or other critical point in all circumstances (often an important safety consideration) then many desired motions may be excruciatingly slow. A decoupled RCM structure positioned so that the motion center coincides with the point where the camera enters the patient's body avoids many of these problems. Each actuator can be sized to produce the desired rate of motion in the corresponding degree of freedom. Furthermore, it is easy to permit more rapid manual positioning of the entire mechanism or of selected subsets of the degrees of freedom by means of manually actuated clutches. In this case, it is important to note that the kinematic constraints imposed by the mechanism prevent inadvertent lateral motions when changing the orientation of the camera.

One embodiment of this concept uses crossed goniometer axes to achieve the requisite decoupling of revolute motions at a remote center. While this embodiment has many advantages, it also has several drawbacks. The principal difficulty is a size/working radius trade off. If a large working radius is desired, then the goniometer axes must be quite large, and the resulting robot structure can become somewhat clumsy and obtrusive in the operating room or can impede access to the patient. If the working radius is small, then the mechanism may get in the way of the surgeon's hands, instruments, or direct vision. A related consideration is that high quality goniometer axes can be expensive and difficult to fabricate.

OBJECTS OF THE INVENTION

An objective of this invention is an improved, compact robot, used to assist surgery, which has an orthogonally decoupled remote center-of-motion and a large working radius.

An objective of this invention is an improved robot, used to assist surgery, which can re-position a surgical instrument in a patient's body while not placing a proximal part of the robot over the patients body in the surgeon's work area.

Another objective of this invention is an improved robot, used to assist surgery, which has all drives on a proximal part of the robot that is kept out of the surgeon's work area.

Another objective of this invention is an improved robot, used to assist surgery, which has all drives on a proximal part of the robot so that the drives are electrically disconnected from a surgical instrument inserted in a patient.

SUMMARY OF THE INVENTION

The present invention is an apparatus that can position and re-position a center-of-motion mechanism at a working point location remote from the apparatus. The apparatus is compact, inexpensive to fabricate, and efficient to adjust. It conveniently permits a surgeon to position the center-of-motion mechanism in a patient at the working point at a distance from the main parts of the apparatus, thereby keeping the main parts out of the surgeon's field of view of the work area and out of the work area in general.

The apparatus has a number of rigid links connected together by pivots, or revolute joints. The rigid links, solely by rotating about these pivots, cause a manipulator structure to constrain the motion of a surgical instrument about a work point a given distance from the apparatus. The links operate together so that the surgical instrument, held by the manipulator, moves about the center-of-motion of the manipulator (which is at the work point) and has orthogonally decoupled degrees of freedom at the work point. Certain links can be made adjustable in length in order to move the center-of-motion of the manipulator without moving the entire apparatus. Adjusting the links also changes the working radius of the apparatus. The links are arranged in such a way so that none of the components of the apparatus, other than those holding the surgical instrument, invade a work area around the instrument. Gravitational forces acting on the apparatus are counter balanced using weights or springs to minimize resistance to apparatus motion.

The apparatus is split into a proximal and distal part, usually at a boundary defined by the points where the parts of an adjustable, rigid linkage are connected together. The proximal part of the apparatus can be adjustably fixed to a stationary object like an operating table. The distal part, which holds the surgical instrument, moves in relation to the proximal part as the adjustable linkages are adjusted. The links can be rotated and adjusted in length by drives that can be controlled either manually or by some controller like a computer. In one embodiment, all the drives are located on the proximal part of the apparatus and electrically isolated from the distal part of the apparatus. This electrical isolation reduces the danger of electrical shock to the patient.

BRIEF DESCRIPTION OF THE DRAWINGS

FIG. 1B shows an embodiment of the present invention having adjustable and separable linkage elements 1 and 2.

FIG. 1C is an exploded view showing the adjustability and separability of the linkage elements.

FIG. 2 shows a counterweight for balancing the manipulator structure against gravitational forces.

FIG. 2A shows counterweights for rebalancing the manipulator structure against gravitational forces when the center of gravity is changed in two degrees of freedom.

FIG. 7A shows an alternative embodiment for driving a surgical instrument on a distal part of the manipulator from a drive on the proximal part of the manipulator.

DETAILED DESCRIPTION OF THE INVENTION

Figure 1:
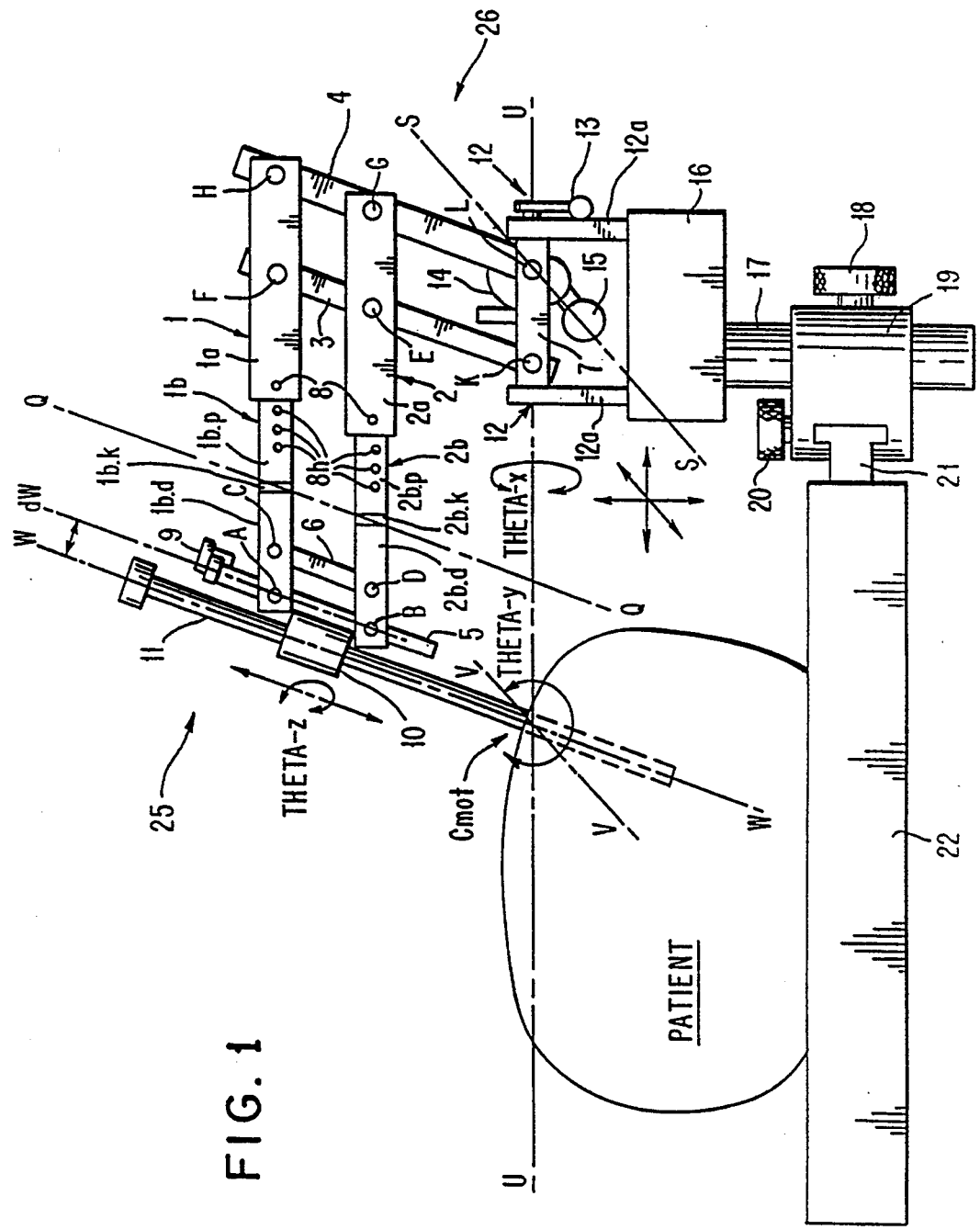
FIG. 1 shows an embodiment of the present invention.
Figure 1A:
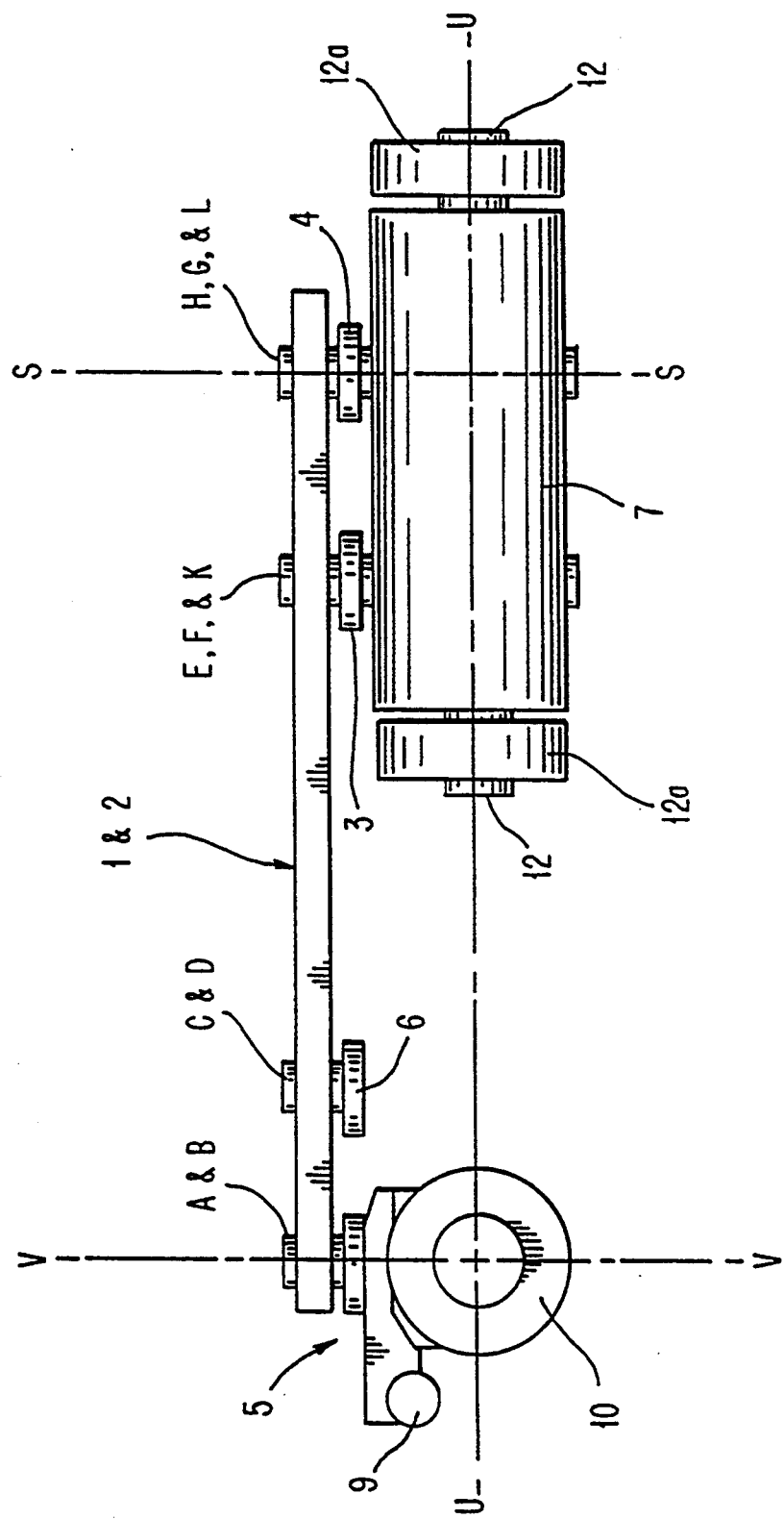
FIG. 1A shows the top view of a preferred embodiment.

FIG. 1 shows an embodiment of tile invention, in which an adjustable remote center-of-motion manipulation system is affixed to an operating table upon which is a patient, and in which the manipulation system holds a laparoscopic camera so that the center of motion is located at the point of entry of the laparoscope into the patient.

In FIG. 1, parallel adjustable telescoping links 1 and 2 are joined to parallel links 3, 4, 5, and 6 by pivot joints A, B, C, D, E, F, G, H, Gimbal link 7 is parallel to links 1 and 2 and is joined to links 3 and 4 by pivot joints K and L. The axes of rotation of pivot joints A-H, and K-L are all parallel and are perpendicular to the plane in which links 1-7 lie. Links 1 and 2 comprise outer members 1a and 2a and inner members 1b and 2b, respectively. The displacement of outer members 1a and 2a relative to their corresponding inner members 1b and 2b is fixed by pins 8 which pass through adjustment holes 8h in members 1b and 2b. In alternative embodiments, brakes, non-backdrivable gears, or other suitable means may be used either to replace or to supplement pins 8 or to provide for continuous modification of the displacement of 1b and 2b relative to 1a and 2a. Member 1b comprises connector 1b.k that divides member 1b into proximal component 1b.p and distal component 1b.d. Similarly, member 2b comprises connector 2b.k that divides it into proximal component 2b.p and distal component 2b.d. Thus it may be seen that connectors 1b.k and 2b.k divide the manipulator into distal components 25 and proximal components 26 along the line QQ. These connectors can comprise a socket type connection with a captive screw or any other known connection used for connecting and disconnecting rigid links. The component containing link 5 is the distal component and the component containing link 3 is the proximal component. In an alternative embodiment, the members 1b and 2b may be left whole and the manipulator may be divided 1s and 2 into proximal and distal components at the telescoping joints between members 1a and 1b and 2a and 2b, respectively.

Link 5 comprises a linear actuator 9, which varies the displacement of revolute actuator 10 along an axis WW parallel to link 5. In one preferred embodiment, this actuator comprises a micrometer lead screw driven by a computer-controlled servo motor or (when the motor power is turned off) by hand. Revolute actuator 10 similarly comprises a computer controlled servomotor, together with a suitable drive mechanism so that it may also be turned by hand if the drive power is off. Revolute actuator 10 carries a surgical instrument 11, which in this case is shown as a laparoscopic camera, and rotates this instrument about an axis of rotation WW parallel to link 5 and is displaced from it by distance dW. We will designate this motion Theta-z. Alternatively, revolute actuator 10 can comprise a holding means for attaching a surgical instrument which can rotate not at all, through a constrained range of angles about axis WW, or continuously about the axis WW.

Gimbal link 7 is joined by rotational joint 12 to carrier member 12a, and rotates about an axis UU parallel to the links 1, 2 and, 7. Axis UU is perpendicular to the rotation axis of pivot joints A–L and intersects axis WW at point Cmot, the work point, at a distance from pivot joint L equal to dW plus the distance from pivot joint A to pivot joint G. Revolute actuator 13 controls the rotational motion Theta-x of gimbal link 7 about rotational joint 12. In one preferred embodiment, actuator 13 is a worm gear, in which the worm head is spring-loaded against the gear teeth and is driven by a computer-controlled servomotor or by hand if the servomotor power is turned off. The worm head may also be pulled away from the gear. Since revolute joint 12 may be fabricated with very low friction, motion Theta-x is essentially unimpeded when the gear head is pulled away, so that the surgeon feels essentially no resistance from the manipulator mechanism to torques he or she exerts on instrument 11 about axis UU. A similar actuator 14 controls the rotation of link 4 about pivot joint L. Since the pantograph-like, multi-link mechanism of links 1–7 guarantees that instrument axis WW remains parallel to link 4, actuator 14 controls the rotation Theta-y of instrument 11 about an axis VV that intersects WW and UU at Cmot. For the case that dW equals zero, this point of intersection Cmot remains fixed. In general, an angular displacement from vertical of $\theta_y$ will produce a lateral displacement of Cmot along UU of $dW \times (1-1/\cos \theta_y)$. In many applications this lateral motion may be small enough to be ignored, especially if dW is very small or $\theta_y$ stays near O. However, it is easy to design the mechanism so that dW is equal to zero. Referring to FIG 1 A, we see the preferred embodiment in which we achieve this by mounting actuator 10 alongside link 5.

Note that UU and VV are perpendicular and that VV and WW are perpendicular. Furthermore, this fact is independent of the nature (or even the presence) of instrument 11 held in the revolute actuator 10, which is the most distal part of the surgical manipulator proper. Thus, the manipulator provides three orthogonally decoupled revolute degrees of freedom resolved at a point Cmot remote from the manipulator structure. Further, the distance from the manipulator actuator 14 controlling motion Theta-y to the corresponding rotation axis VV can be changed by adjusting the length of telescoping links 1 and 2.

Note also that the effective "working radius" of the most distal part of the manipulator (i.e., revolute actuator 10) from the center of motion Cmot may be modified by moving linear actuator 9. In other embodiments much the same thing can be accomplished by replacing links 3 and 4 by telescoping links similar to 1 and 2.

In FIG. 2, counterweight 15 balances the torques exerted by gravitational forces on the manipulator structure whenever axis WW is not vertical. This is advantageous both to reduce the torque required of actuators 13 and 14 and to permit greater manipulation ease when the actuators are disengaged. Although for a given counterweight mass and position, the balance is only perfect for one particular load mass and position of linear joint 9, the differences are small enough so that they can be ignored in many applications. If they are significant, an adjustment is easily provided. For example, counterweight 15 may be mounted on a screw axis 15a. Increases in the load mass or increases in the working radius would be compensated for by increasing the distance of counterweight 15 from gimbal link 7. One difficulty of this arrangement is that, while it compensates for changes in effective working radius or shifts in the center-of-mass of instrument 11 along the axis WW, it does not compensate for the torque about SS of changes in instrument mass. However, additional adjustments are easily provided, as in FIG. 2A. Here, an additional mass 15b is advanced along screw axis 15c, which is perpendicular to link 4. Increases in an instrument mass or other changes of the center of gravity in the plane perpendicular to the pin axes A–L may thus be compensated by moving weights 15 and/or 15b further along their respective adjustment screw axes 15a and 15c. An additional weight, not shown, affixed to link 4 on a screw axis parallel to pin axes A–L may be added to compensate for changes in the load center of gravity out of the plane if required. Preferably, these counterweights should be adjusted so that the total center of gravity of the manipulator and instrument coincided with a point on the line UU. More preferably, this point will be at the intersection of line UU and pivot axis L.

Figure 3:
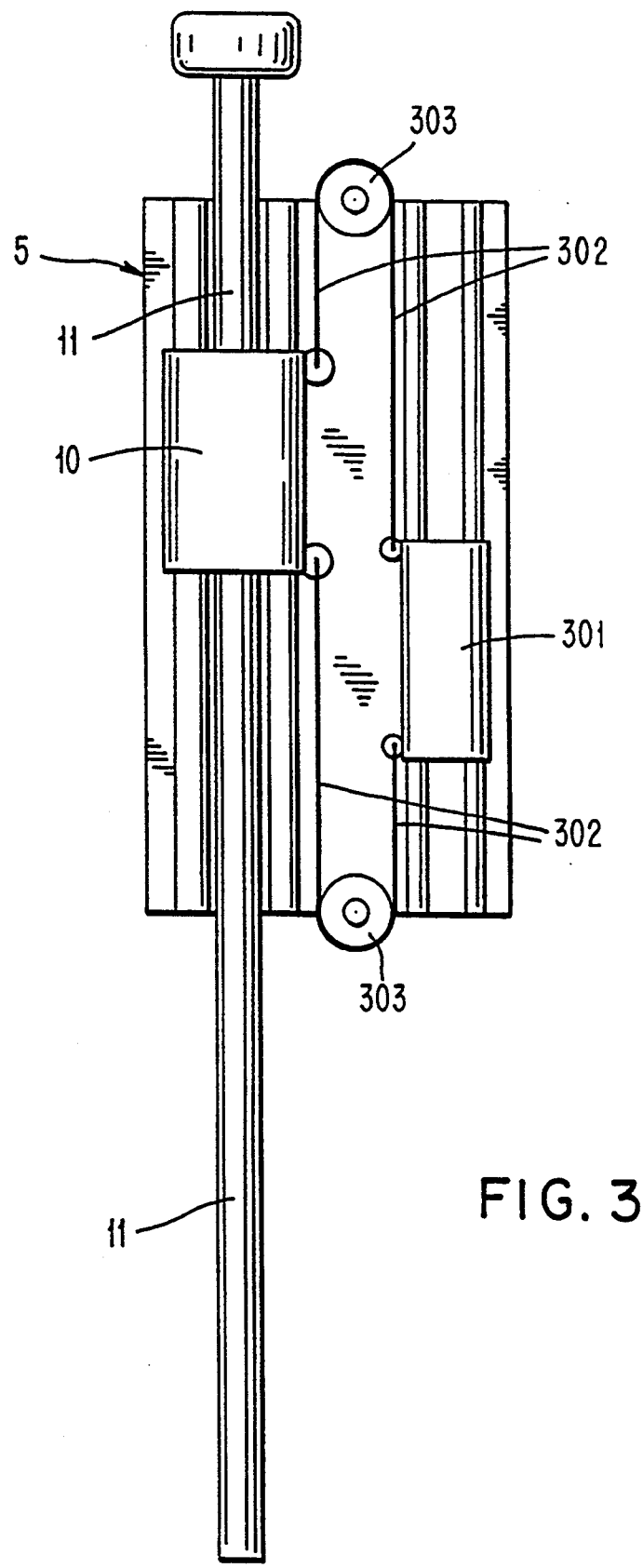
FIG. 3 shows a counterweight apparatus for balancing the weight of a surgical instrument and an actuator that moves it.

An alternative embodiment for compensating for changes in working radius is shown in FIG. 3. In this case a counterweight 301, equal in mass to revolute actuator 10 plus instrument 11 slides along link 5 and is attached to actuator 10 by wires 302 and pulleys 303 so that it moves in a direction opposite to actuator 10, thus maintaining a constant center of mass.

Figure 4:
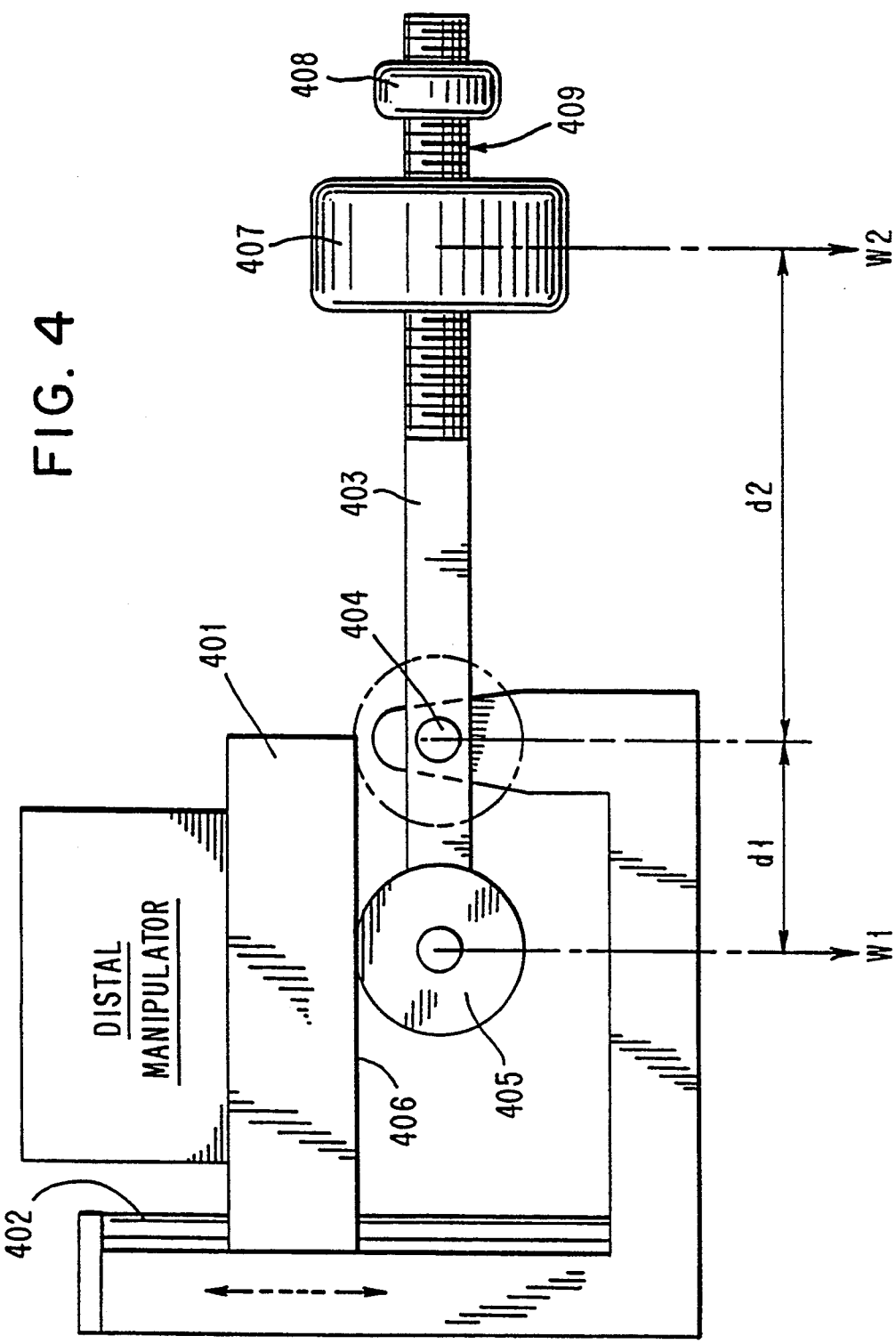
FIG. 4 shows a counterweight system attached to the manipulator stage to compensate for the weight of the manipulator structure.

Referring again to FIG. 1, carrier member 12a is affixed to a conventional XYZ stage 16, which in one preferred embodiment comprises three linear stages (X, parallel to axis UU, Y, parallel to VV, and Z, perpendicular to both X and Y). Each linear stage further comprises a linear actuator similar to the linear actuator 9. If desired, a constant force spring may be attached to the Z stage to compensate for the weight of the manipulator structure. Alternatively, a counterweight system such as that shown in FIG. 4 may be used. Referring to FIG. 4, we see a moving Z-stage component 401 running on bearing rails 402, with a total weight W1. Link 403 pivots on pivot joint 404. A roller 405 at distance D1 rolls on a horizontal bottom surface 4.06 of Z stage component 401. A counterweight 407, with weight W2 is located at the other end of link 403 at a distance D2 equal to $D1 \times W1/W2$ A second (smaller) counterweight 408 with distance adjusting means 409 (here shown as a screw axis) is used to compensate for small additions or subtractions to the load (e.g., by installing or changing instrument 11). If desired, this adjustment may also be accomplished by moving counterweight 407.

Referring again to FIG. 1, XYZ stage 16 is affixed to a vertical linear member 17, which slides vertically in member 19 and may be locked in any convenient position by locking member 18. Once again, constant force springs and/or counterweights optionally may be used to compensate for the weight of the manipulator and load. In one preferred embodiment, these springs have slightly greater force than the manipulator weight, so that if the locking member is loosened the manipulator will be lifted up away from the patient. Member 19 may be locked by lock member 20 to a rail 21 affixed to the operating table 22, along which member 19 slides.

In the embodiment shown, the length of telescoping links 1 and 2 are held fixed by pins 8, and the adjustment is used for approximate positioning of the center of motion, along with members 17–20. Fine adjustment of the position of the remote center-of-motion is accomplished by the XYZ stage. The auxiliary link 6 holds the distal telescoping members 1b and 2b parallel when the pins 8 are removed so that 1b and 2b are free to slide in 2a and 2b. This facilitates the telescoping. So long as links 1 and 2 do not form a right angle with links 3-6, link 5 will remain parallel to link 4 even when the pins are disengaged. Thus, for coarse adjustment it is important for the surgeon to be sure that the coarse adjustment is not performed when these links are at right angles, and to be sure that the pins are placed into the proper holes when adjustment is complete. This condition may be guaranteed at some loss of work volume simply by mechanically constraining the links so that they cannot reach right angles. Two further advantages of the use of telescoping links 1 and 2 for adjusting the position of Cmot along UU are (i) the mechanism requires less "backing up" space away from the operating table, and (ii) the distal parts of the mechanism can be readily removed for sterilization, while the more proximal parts can be covered with sterile drapes. Furthermore, several different instances of the distal structure, equipped with different distal actuators and instrumentation and/or with different lengths of members 1b and 2b may be provided quite simply.

Figure 5:
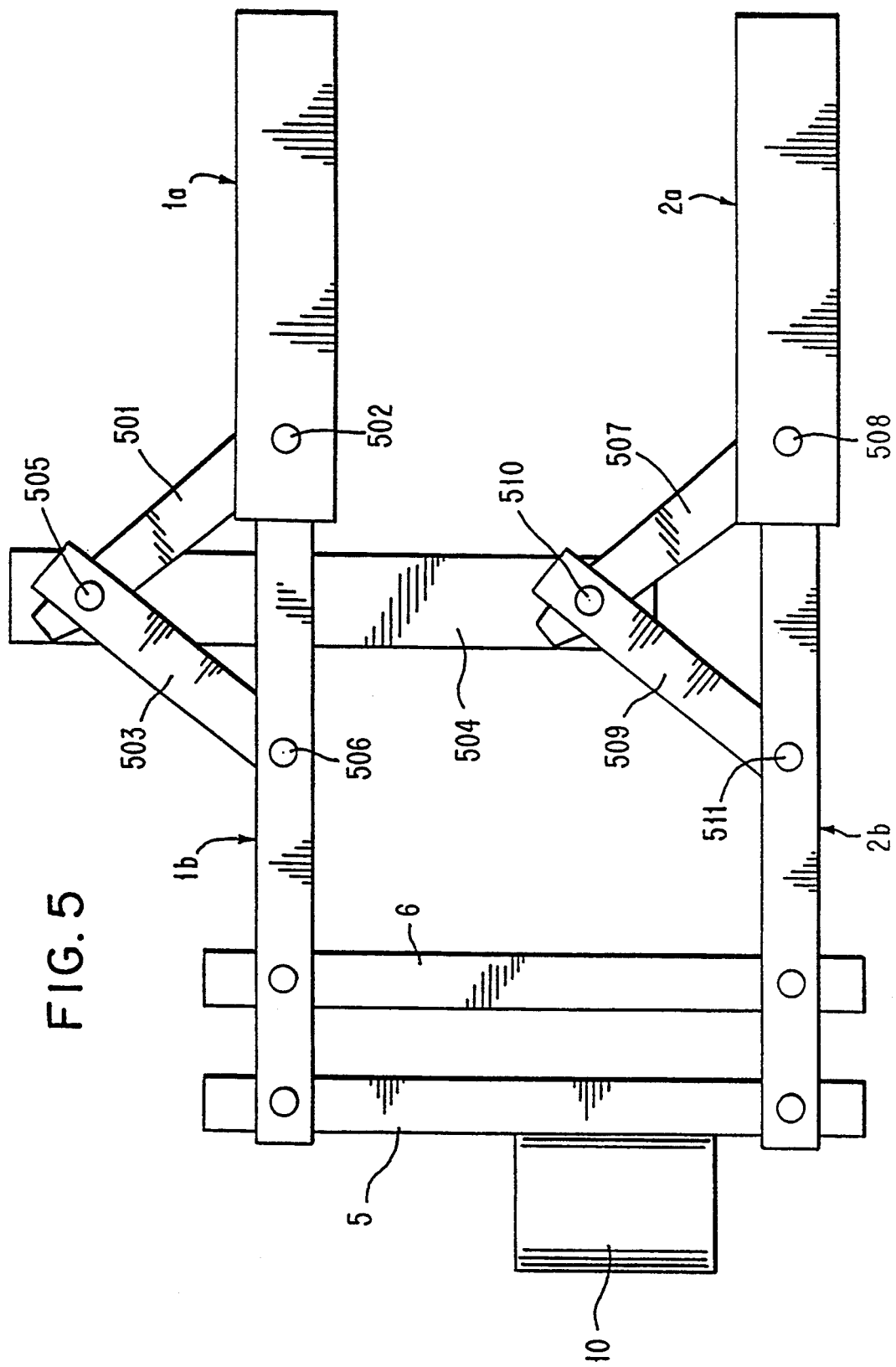
FIG. 5 shows a mechanical linkage used to insure that telescopic elements of a parallel linkage move at equal amounts.

In other embodiments, the telescoping links may be fitted with manual or computer controlled micrometer adjustments and used to provide fine positional adjustment. So long as links 1 and 2 never attain a right angle with links 3-6, only one telescoping link needs to be driven; the other link can simply follow along idly. If a right angle is possible, additional elements are needed to guarantee that both 1b and 2b move in the same direction. One mechanical linkage to accomplish this task is illustrated in FIG. 5. Here, link 501 is attached to member 1a at pivot joint 502 and to links 503 and 504 at pivot joint 505. Link 503 is attached to member 1b at pivot joint 506. Similarly link 507 is attached to member 2a at pivot joint 508 and to links 509 and 504 at pivot joint 510. Link 509 is attached to member 1b at pivot joint 511. In this embodiment, the lengths of links 501, 503, 507, and 509 are all the same.

To see how this mechanism guarantees that members 1b and 2b must always move in the same direction, consider a situation in which member 1b is moving "out", and member 2b is moving "in"; then the angle made by links 501 and 503 is becoming more shallow, while the angle between links 507 and 509 is becoming more acute. But this would change the distance between pivot joints 505 and 510, which is held fixed by link 504. So link 1b cannot move "out" while 2b moves "in" Since the situation is symmetrical, 1b and 2b must move in the same direction. Clearly, this mechanism may also be used to properly constrain an adjustment procedure in which telescoping links 1 and 2 may be at right angles to links 3-6.

Figure 6:
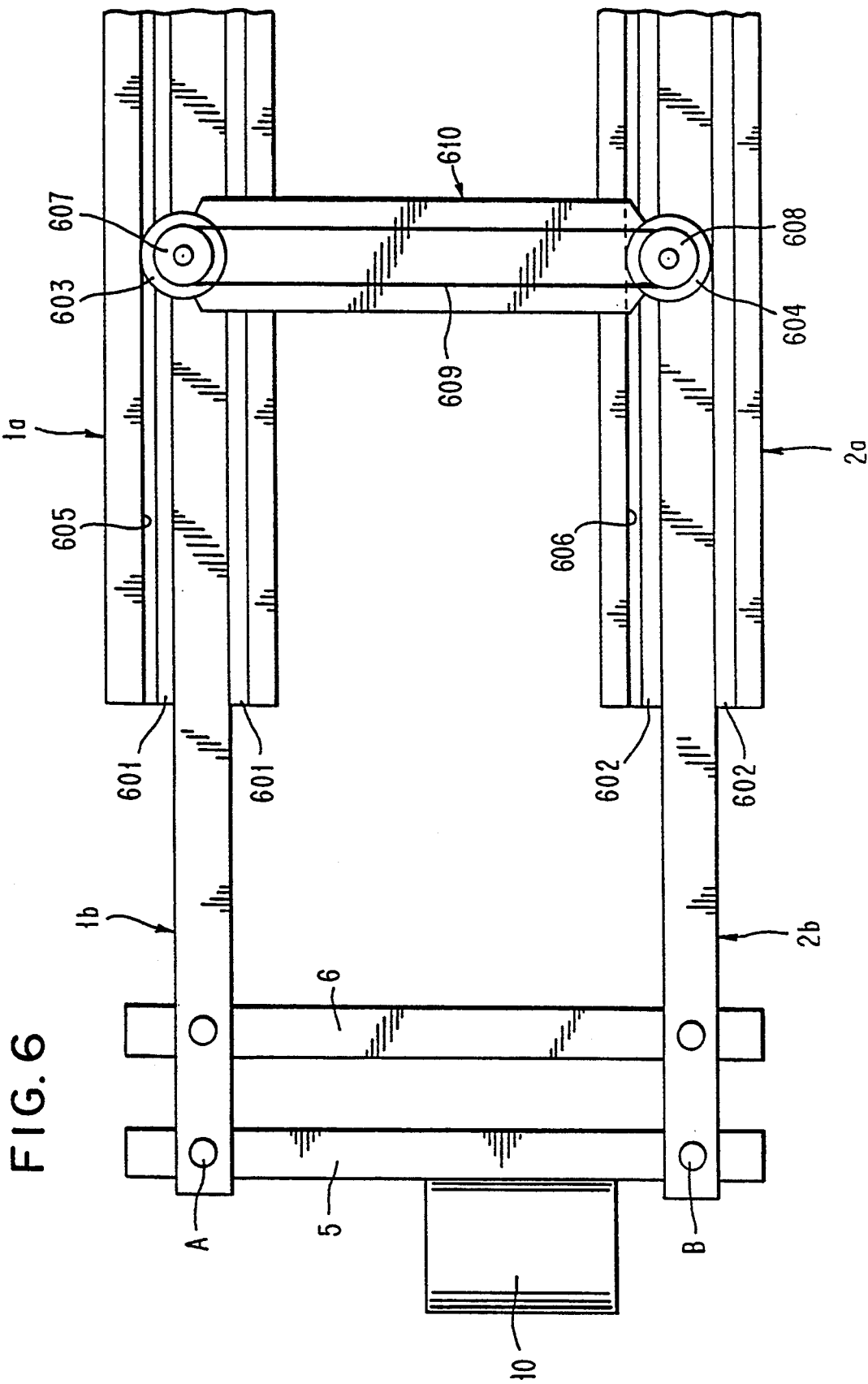
FIG. 6 is an alternative embodiment performing the function shown in FIG. 5.

An alternative embodiment is shown in FIG. 6. In this embodiment, members 1a and 2a of link arms 1 and 2 comprise linear bearing elements 601 and 602, respectively, along which members 1b and 2b slide. Members 1b and 2b also comprise roller elements 603 and 604, respectively, which are constrained to roll without slipping on rolling surfaces 605 and 606 of members 1a and 2a, respectively. This constraint may be achieved by the use of high friction materials with preloading, by zero-backlash rack-and-pinion elements, or by any other convenient means known in the engineering art. The distances from tile rotation axes of roller elements 603 and 604 to pivot joints A and B, respectively, are identical. Roller elements 603 and 604 also comprise pulleys 607 and 608, respectively. Pulleys 607 and 608 are connected by a non-slip flexible belt 609 and are separated at a constant distance equal to the distance between pivot joints A and B. Link 610 thus provides additional support maintaining the parallelism of link members 1b and 2b, so that link 6 may optionally be eliminated. Any convenient means known in the engineering art may be used to prevent belt 609 from slipping on pulleys 607 and 608. One such method would be to use toothed pulleys and a toothed timing belt. Another would simply be to use high friction materials and sufficient tension on the belt. It may be readily seen that the rotation of pulleys 607 and 608 and (thus) of rollers 603 and 604 are identical. Since rollers 603 and 604 cannot slip relative to rolling surfaces 605 and 606, which are part of members 1a and 2a, rollers 603 and 604 must displace by the same amount relative to members 603 and 604. Since rollers 603 and 604 are affixed to members 1b and 2b, it follows that members 1b and 2b must move by the same amount relative to members 1a and 2a. With this arrangement, it is also quite easy to provide continuous adjustment of the length of links 1 & 2 by equipping one of the rollers with a manual or computer-controlled drive mechanism like a crank handle or servomotor, with whatever gearing is desired to provide a suitable mechanical advantage.

Figure 1D:
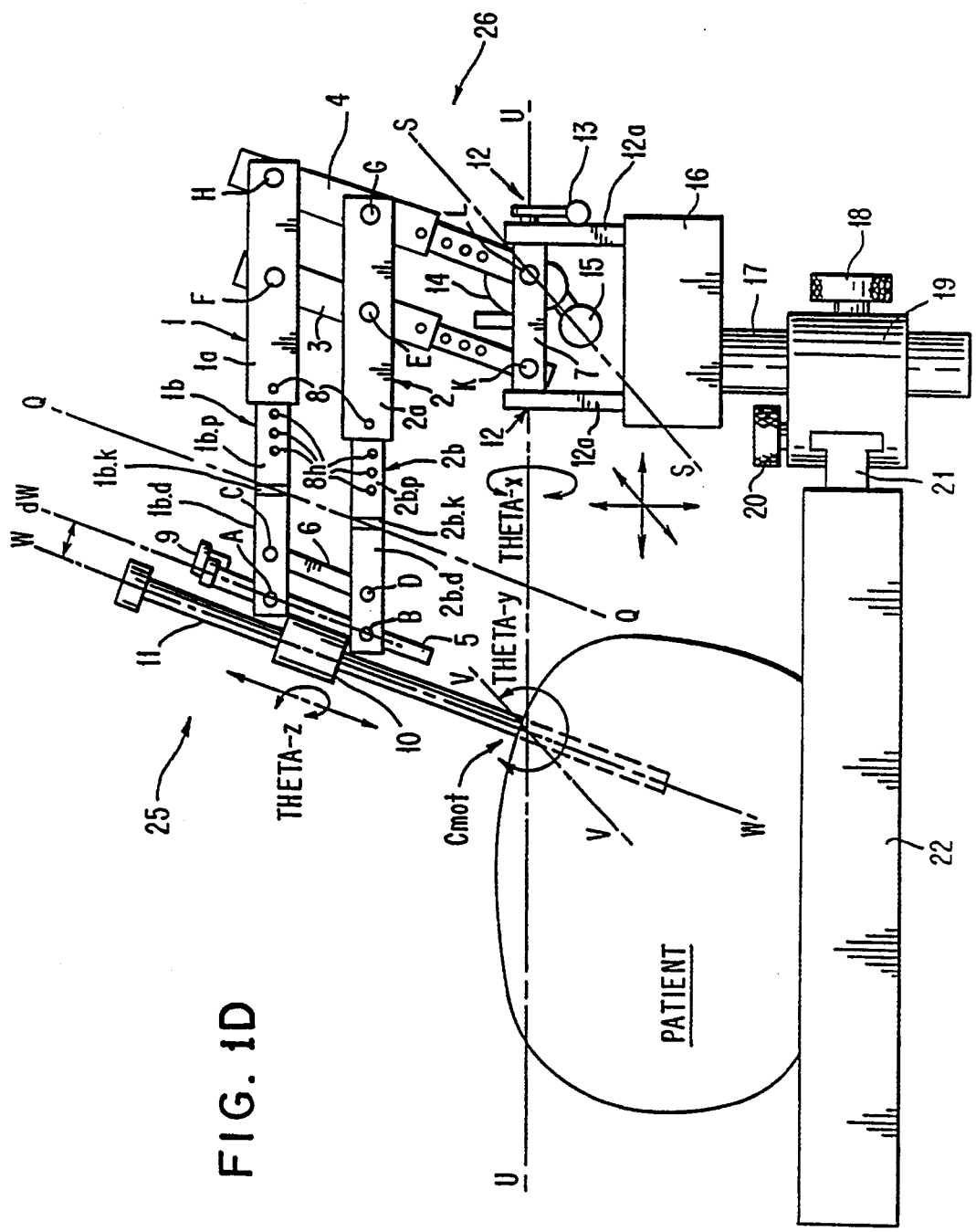
FIG. 1D shows an embodiment of the present invention having adjustable linkage elements 3 and 4.

It may also be readily seen that similar methods may be used to provide continuous adjustments to tile lengths the sections of links 3 and 4 proximal to links 1 and 2. See FIG. 1D. In this case, actuator 9 may be removed from link 5, since substantially the same adjustment may be achieved by altering the lengths of the proximal sections of links 3 and 4. This can have substantial benefits for the simplicity, ease-of-sterilization, and compactness of the distal parts of the manipulator, especially if actuator 10 can be replaced by a simple tool holder or guide, as may often be done for biopsy applications. Note, also, that altering the lengths of the proximal sections of links 3 and 4 has the further advantage that the distance above the working point Cmot of links 1 and 2, as well as the most distal part of the manipulator (actuator 10) can be altered.

It should be noted that changing the length of links 1 and 2 or of links 3 and 4 will, in general, shift the center-of-gravity of the rotating portion of the mechanism. This may be readily compensated for by changes in the displacement of counterweights 15 and 15b. Such changes may be performed manually, by means of computer controlled actuators, or by mechanical means coupled to the motion of the links.

Because non-backdrivable transmission elements are used in actuators 9, 10, 13, 14, and in XYZ stage 16, forces applied to the surgical instrument 11 will not be transmitted to the drive motors and (even if the motors are turned off) will result in no net motion of the instrument. In alternative embodiments, in which active control of the forces exerted by a surgical instrument on the patient may be desired, these transmission elements may be replaced by backdrivable transmission elements such as ball-screws, low friction rack-and pinions, belts, direct coupling, or the like so that forces applied to the instrument will be transmitted with little loss back to the drive motors. Furthermore, because of the orthogonal decoupling, forces or torques aligned with individual degrees of freedom will be transmitted to individual motors. Similarly, forces or torques exerted by individual motors will be transmitted with little loss to the instrument, with no coupling at the remote center-of-motion. Since the structure itself may be counterbalanced to correct for all gravitational loading on the structure or instrument, and since safety considerations usually require that motions be slow enough that inertial effects are very small, the actuators may be sized with regard only to the maximum force/torque desired to be exerted on the patient by the instrument, resolved at the center-of-motion. Furthermore, the decoupling greatly simplifies control.

If computer-controlled, or manually actuated brakes are substituted for the drive motors, and backdrivable transmission elements are used, then the mechanism permits selective locking of degrees of freedom. In this case, the surgeon would be able to manipulate the surgical instrument with little or no impedance in any unlocked degree-of-freedom, but would not be able to move it in any locked degree of freedom. This capability greatly facilitates tasks in which the instrument must be placed in precise alignment with the patient or with other objects in the operating room or in safety considerations require that motion in some degrees of freedom be prevented temporarily. If clutching mechanisms are used to engage/disengage the drive actuators from their corresponding joints, then it is quite easy to provide for selectable free motion vs computer (or human) controlled line motion in individual degrees of freedom. For example, if revolute actuators 13 and 14 are implemented as worm gears, then the worm heads may be spring-loaded to hold them against the gears. When engaged, the worm gears permits a computer or manually controlled fine adjustment of the corresponding revolute degrees of freedom Theta-x and Theta-y. If a head is pulled away from the gear teeth, then that degree-of-freedom is capable of rapid free motion in response to forces exerted (by the surgeon) on the surgical instrument. This capability is especially useful in permitting rapid coarse adjustment by the surgeon with complete tactile feedback through the surgical instrument, followed by a slower micrometer fine adjustments to achieve a desired positional goal.

In many surgical applications, it is desirable for tile entire distal part of the manipulator to be removable for sterilization or to accommodate different end effectors or substantially different lengths for members 1a and 1b. This may easily be accomplished by separating (1s and 2s) the manipulator into proximal and distal components at the 1a–1b and 2a–2b interface of links 1 and 2 respectively. In an alternative embodiment, described above, the separation can take place at connectors 1 b.k and 2b.k.

Figure 7:
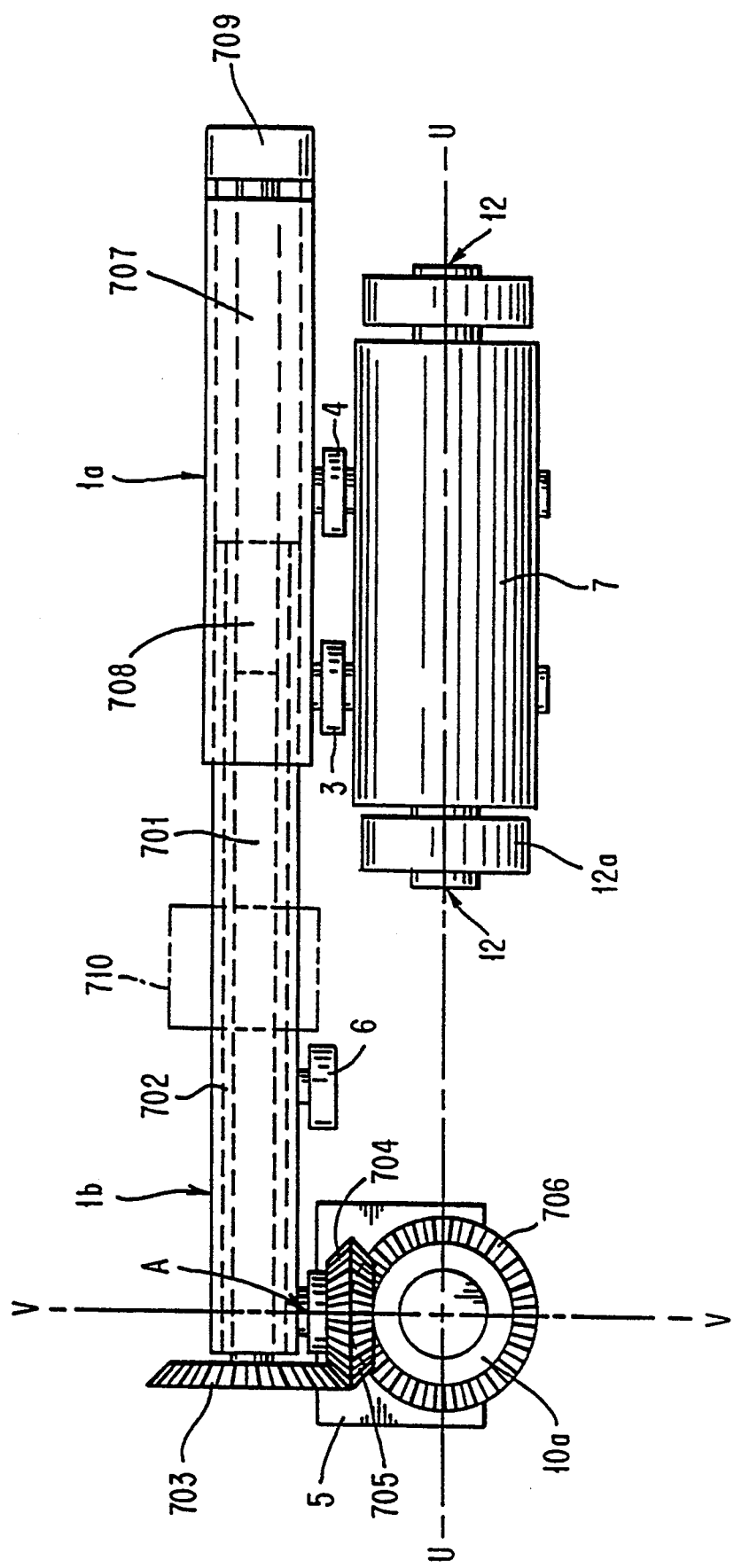
FIG. 7 shows an embodiment for driving a surgical instrument on a distal part of the manipulator from a drive on the proximal part of the manipulator.

It is also often very desirable for the distal parts of the manipulator to contain no electrical components and, indeed, to contain no electrically conductive or metal parts. This is readily accomplished by tile use of composite and/or ceramic materials for the distal mechanism, with tile exception of distal actuators 9 and 10. The action of distal actuator 9 may be replaced by the use of adjustable telescoping links for links 3 and 4. Referring now to FIG. 7, we see how actuator 10 may be powered by a computer controlled motor mounted on the proximal manipulator. In FIG. 7, actuator 10 has been replaced by a passive instrument carrier 10a, which is attached by suitable bearings to link 5 so that it is free to rotate about an axis perpendicular to UU and VV. Distal member 1b comprises an inner rotating member 701. Member 1b also comprises an inner bearing or sleeve 702 in which member 701 rotates and which captures member 701 so that it cannot slide along member 1b. Member 701 comprises a bevel gear 703 which engages a bevel gear 704 mounted coaxially to pivot joint A. Bevel gear 704 is rigidly affixed to bevel gear 705, which engages bevel gear 706 mounted on distal instrument carrier 10a. In this embodiment, distal instrument carrier 10a contains no active elements, but simply turns in suitable bearings, which may be made of nylon, composite materials, ceramics, or any other suitable materials, as are the gears 703–706. Member 1a comprises a rotating member 707 coaxial to member 701 and slidably connected to member 701 by means of a spline coupling 708 or other methods known in the art which guarantee that member 701 rotates in synchrony with member 707. Member 707 is driven by a computer controlled servomotor 709. If desired, computer controlled servomotor may be replaced by a manually driven crank or other device.

It should be noted that drive cables and turning pulleys or other means known to the art may be readily substituted for bevel gears 703–706 as means for converting the rotation of member 701 to the rotation of distal instrument carrier 10a.

It should also be noted that the embodiment comprising bevel gears 703–706, described above, couples the rotational motions about axes VV and WW. I.e., whenever link 5 rotates about pivot joint A, then instrument carrier 10a will rotate about axis WW. This coupled motion may, of course, be compensated for by suitable rotations of member 707. However, the rotations may be uncoupled by alternative embodiments for transmitting rotational torques through a changing angle. One simple solution would be to eliminate bevel gears 703–706, and (instead) to drive instrument carrier 10a through a flexible shaft 711 connected to a worm gear drive 712 on instrument carrier 10a. See FIG. 7A.

From this discussion, it may be readily seen that all drive elements and electrical components may readily be accommodated on the proximal section of the manipulator. It may be further seen that no distal component requires electrical power or even the presence of conductive or metal parts, thus simplifying sterilization, electrical safety, compatibility with medical imaging devices like computed tomography (CT) and magnetic resonance imaging (MRI), and further reducing the bulk of the distal portions of the manipulator.

If simply electrical isolation is desired, this may be readily accomplished by fabricating a single section 710 of member 1a and a similar section of member 2a out of non-electrical materials. Such sections may be designed to be used as an alternative quick-disconnect place for the distal manipulator, thus permitting the telescoping components of links 1 and 2 to remain fixed to the proximal manipulator, with consequent simplifications in design. In one embodiment this section 710 may comprise connectors 1 b.k and 2b.k.

If hydraulic actuators are used, the entire manipulator can be fabricated from electrically non-conductive materials. Servo valves can be mounted off the manipulator so no electric power is brought to the manipulator and no conductive components are on or near the manipulator. Since all motions are relatively slow, any compliance in the hydraulic fluid or hoses need not create a significant control problem. As an alternative to servo valve drives, the hydraulic system can be driven in a fixed volume manner by remote cylinders by methods known in the art. Alternatively, electrically non-conductive flexible shafts may be used to transmit drive power to the manipulator. Similarly, pneumatic actuators or other non-conductive actuators can be used. If computer control motion of the manipulator is not needed, simpler embodiments can be fabricated by using electrically non-conductive elements like micrometers, linkages, etc. Such manipulator designs eliminating electric actuator and/or electrically conductive components are especially useful when the manipulator is to use in conjunction with magnetic resonance imaging (MRI) systems.

We claim:

1. A manipulator apparatus, for assisting surgery, comprising:
   a rotational joint that permits a first direction of revolute motion about a first axis;
   a linkage comprising rigid linkage elements connected by two or more pivots with a second direction of revolute motion about the two or more pivots, the pivots having rotating axes parallel to one another, one or more of the two or more pivots being distal attachment pivots and one or more of the two or more pivots being proximal attachment pivots, the axis of each pivot being perpendicular to the first axis and the linkage being connected to the rotational joint at one or more of the proximal attachment pivots, the rotational joint permitting the linkage to rotate about the first axis;
   a linear actuator connected to the linkage at one or more of the distal attachment pivots, the linear actuator having a third axis being perpendicular to the pivot axes; and
   a connection attached to the linear actuator for attaching a surgical instrument to the linear actuator, the instrument having an instrument axis adapted to be parallel to the third axis, the linear actuator for moving the instrument along the instrument axis to enter a patient at a work point on the patient,
   where the first axis and the third axis intersect at the work point, the work point being remote, at a first approximately fixed distance, from at least one proximal attachment pivot axis, the linear actuator modifying a second approximately fixed distance from the instrument to the work point and maintaining the instrument axis parallel to the third axis during a rotation in the first and second directions of revolute motion.

2. A manipulator apparatus, for assisting surgery, as in claim 1, where the first and second approximately fixed distances are exact fixed distances.

3. A manipulator apparatus, for assisting surgery, as in claim 1, where the linear actuator.

4. A manipulator apparatus, for assisting surgery, comprising:
   a rotational joint that permits a first direction of revolute motion about a first axis;
   a linkage comprising rigid linkage elements connected by two or more pivots, the linkage elements including a proximal element and a distal element, the proximal element having a first end connected to a first end of the distal element, a second end of the proximal element connected to the rotational joint at one or more proximal pivots of the two or more pivots thereby permitting the linkage to rotate about the first axis, a second end of the distal element connected to a linear actuator at one or more, distal pivots of the two or more pivots the linkage elements having a second direction of revolute motion about an axis of each pivot, each pivot axis being perpendicular to the first axis and the linear actuator having a third axis being perpendicular to the pivot axes; and
   a connection attached to the linear actuator for attaching a surgical instrument, the instrument having an instrument axis adapted to be parallel to the third axis, and the linear actuator for moving the instrument along its instrument axis to enter a patient at a work point;
   where the first axis and the third axis intersect at the work point, the work point being remote, at a first approximately fixed distance, from at least one proximal pivot, the linear actuator modifying a second approximately fixed distance from the work point and maintaining the instrument axis parallel to the third axis during a rotation in the first and second direction of revolute motion.

5. A manipulator apparatus, for assisting surgery, as in claim 4, where the rotation of the linkage elements is driven by a linkage actuator.

6. A manipulator apparatus, for assisting surgery, as in claim 5, where the linkage actuator can be decoupled.

7. A manipulator apparatus, for assisting surgery, as in claim 5, where the linkage actuator is located on the proximal element, the proximal element being electrically isolated from the distal element.

8. A manipulator apparatus, for assisting surgery, as in claim 4, where the rotation of the linkage elements is driven manually.

9. A manipulator apparatus for assisting surgery, as in claim 4, where one or more of the linkage elements can be separated, at a disconnect, into a first element section and a second element section whereby the manipulator apparatus is separable into a distal part having the linear actuator and a proximal part.

10. A manipulator apparatus for assisting surgery, as in claim 9, where the disconnect is made from an electrically non-conductive material.

11. A manipulator apparatus for assisting surgery, as in claim 4, where at least one of the linkage elements is made of an electrically non-conducting material so that the manipulator apparatus includes a distal part having the linear actuator and a proximal part, the distal part being electrically isolated from the proximal part.

12. A manipulator apparatus for assisting surgery, as in claim 4, where all the components of the manipulator apparatus are fabricated from non-conductive materials.

13. A manipulator apparatus, for assisting surgery, comprising:
   a rotational joint that permits a first direction of revolute motion about a first axis;
   an adjustable linkage comprising linkage elements connected by two or more pivots, the linkage elements including a proximal element and a distal element, the proximal element having a first end connected to a first end of the distal element, a second end of the proximal element connected to the rotational joint at one or more proximal pivots of the two or more pivots, thereby permitting the linkage to rotate about the first axis, a second end of the distal element connected to a holding means at one or more distal pivots of the two or more pivots, the linkage elements having a second direction of revolute motion about an axis of each pivot, each pivot axis being perpendicular to the first axis, holding means having a third axis being perpendicular to the pivot axes; and
   a connection attached to the holding means for attaching a surgical instrument, the instrument having an instrument axis adapted to be parallel to the third axis;

where the first axis and the third axis intersect at a work point, the work point being at a remote position at a first approximately fixed distance from at least one proximal pivot, the holding means for moving the surgical instrument along the instrument axis; and maintaining the instrument axis parallel to the third axis during a rotation in the first and second direction of revolute motion.

14. A manipulator apparatus, for assisting surgery, as in claim 13, where one or more of the linkage elements is adjustable in length and the length adjustment changes a second approximately fixed distance between the holding means and the work point.

15. A manipulator apparatus, for assisting surgery, as in claim 14, where the length adjustment is a telescopic linkage.

16. A manipulator apparatus, for assisting surgery, as in claim 13, where one or more of the linkage elements is adjustable in length and the length adjustment changes the first approximately fixed distance.

17. A manipulator apparatus, for assisting surgery, as in claim 16, where the length adjustment is a telescopic linkage.

18. A manipulator for assisting surgery, as in claim 13, where the proximal clement is a set of proximal parallel elements and the distal element is a set of distal parallel elements, the linkage being adjustable due to the lengths of the set of proximal parallel elements being adjustable in length in a manner that maintains the proximal parallel elements parallel, and adjusting the proximal element length changes the second approximate fixed distance between the holding means and the workpoint.

19. A manipulator for assisting surgery, as in claim 18, where the set of proximal parallel elements are constrained to move in tandem by identical amounts.

20. A manipulator for assisting surgery, as in claim 18, where the set of proximal parallel elements are adjusted in length by telescoping.

21. A manipulator for assisting surgery, as in claim 20, where the telescoping proximal parallel elements can be separated, the first ends of proximal parallel elements being detachable from the second ends of the proximal parallel elements so that the holding means can be separated from the remainder of the manipulator.

22. A manipulator apparatus for assisting surgery, as in claim 13, where two or more of the linkage elements is a set of parallel elements, the linkage being adjustable due to the lengths of the set of parallel elements being adjustable in length in a manner that maintains the parallel elements parallel, and adjusting the length of the parallel elements changes the first approximately fixed distance.

23. A manipulator apparatus for assisting surgery, as in claim 22, where the parallel elements in the set of parallel elements are constrained to move in tandem by identical amounts.

24. A manipulator apparatus for assisting surgery, as in claim 22, where the parallel elements in the set of parallel elements are adjusted in length by telescoping.

25. A manipulator apparatus for assisting surgery, as in claim 24, where the telescoping parallel elements can be separated, so that the third holding means and the surgical instrument can be separated from the remainder of the manipulator.

26. A manipulator apparatus, for assisting surgery, as in claim 13, where the lengths of at least one of the linkage elements is adjustable by an adjustment actuator.

27. A manipulator apparatus, for assisting surgery, as in claim 13, where the rotation of the linkage elements is driven by a linkage actuator.

28. A manipulator apparatus, for assisting surgery, as in claim 27, where the linkage actuator can be decoupled.

29. A manipulator apparatus, for assisting surgery, as in claim 13, where the rotation of the linkage elements is driven manually.

30. A manipulator apparatus for assisting surgery, as in claim 13, where one or more of the linkage elements can be separated, at a disconnect, into a first element section and a second element section whereby the manipulator apparatus is separable into a distal part having the linear actuator and a proximal part.

31. A manipulator apparatus for assisting surgery, comprising:

a rotational joint with a first direction of rotation about a first axis;

a linkage having linkage elements, the elements having a second direction of rotation about two or more pivots, one or more of the pivots being distal attachment pivots and one or more of the pivots being proximal attachment pivots, a rotating axis of each pivot being perpendicular to the first axis and the linkage being connected to the rotational joint at one or more of the proximal attachment pivots to permit rotation of the linkage about the first axis;

a linear actuator connected to the linkage at one or more of the distal attachment pivots, the linear actuator having a third axis being perpendicular to the distal attachment pivot axes;

a connection attached to the linear actuator for attaching a surgical instrument to the linear actuator, the instrument having an instrument axis adapted to be parallel to the third axis and adapted to pass through a work point; and a mounting means for connecting the manipulator apparatus to a fixed surgical structure, where the first axis and the third axis intersect at the work point, the work point being remote, at a first approximately fixed distance, from at least one proximal attachment pivot axis, the linear actuator modifying a second approximately fixed distance from the work point and maintaining the instrument axis parallel to the third axis during rotation in the first direction and second direction of revolute motion.

32. A manipulator apparatus for assisting surgery, as in claim 31, where the mounting means is one or more linear displacement stages.

33. A manipulator apparatus for assisting surgery, as in claim 31, where the weight of the apparatus is counterbalanced in at least one direction of rotation by a counterbalancing means for reducing the gravity force on the surgical instrument.

34. A manipulator apparatus, for assisting surgery, as in claim 33, where the counterbalancing means comprises a weight.

35. A manipulator apparatus, for assisting surgery, as in claim 34, where the counterbalancing means comprises an adjustable weight.

36. A manipulator apparatus, for assisting surgery, as in claim 35, where the adjustable weight comprises one weight for a coarser adjustment and a second weight for a finer adjustment.

37. A manipulator apparatus, for assisting surgery, as in claim 35, where there are a plurality of weights used to adjust the balance of the manipulator in a plurality of directions.

38. A manipulator apparatus for assisting surgery, as in claim 31, where the mounting means is adjustable.

39. A manipulator apparatus for assisting surgery, as in claim 31, where the fixed surgical structure is an operating table.

40. A manipulator apparatus for assisting surgery, as in claim 31, where the mounting means comprises a slidable locking means adjustably connecting the manipulator to a fixed element on the surgical structure.

41. A manipulator apparatus for assisting surgery, as in claim 40, where the fixed element is a rail.

* * * * *